United States Patent [19]
Hicks

[11] Patent Number: 5,372,576
[45] Date of Patent: Dec. 13, 1994

[54] THERAPEUTIC FOOT ORTHOSIS

[75] Inventor: Rickey L. Hicks, St. Petersburg, Fla.

[73] Assignee: Orthosis Corrective Systems Corp., Pinellas Park, Fla.

[21] Appl. No.: 75,213

[22] Filed: Jun. 10, 1993

[51] Int. Cl.$^5$ ................................................ A61F 5/00
[52] U.S. Cl. ...................................... 602/27; 602/23; 128/882
[58] Field of Search ................. 602/5, 6, 7, 23, 27–29; 128/882

[56] References Cited

U.S. PATENT DOCUMENTS

| | | |
|---|---|---|
| Re. 33,762 | 12/1991 | Lonardo . |
| 3,345,654 | 10/1967 | Noble .................... 602/27 X |
| 4,554,912 | 11/1985 | Haberman ................. 602/27 |
| 5,020,523 | 6/1991 | Bodine ...................... 602/27 |
| 5,088,479 | 2/1992 | Detoro ...................... 602/27 |
| 5,088,480 | 2/1992 | Wang ..................... 602/27 X |
| 5,143,058 | 9/1992 | Laber et al. ................ 602/28 |
| 5,151,081 | 9/1992 | Williams .................... 602/27 |
| 5,154,695 | 10/1992 | Farris et al. ................ 602/27 |
| 5,197,942 | 3/1993 | Brady ..................... 602/23 X |

Primary Examiner—Stephen R. Crow
Assistant Examiner—Linda C. M. Dvorak
Attorney, Agent, or Firm—Herbert W. Larson

[57] ABSTRACT

A therapeutic device for attachment to the foot and leg of a user for alleviating and correcting foot deformities, and for maintaining the foot in a fixed, stable, yet comfortable position following surgery or other medical procedure performed on the foot. The device comprises a leg engaging portion, a foot supporting portion and a heel portion which interconnects and advantageously is integral with the leg and foot portions. The heel portion has an inner and an outer surface and a curvature such that the inner surface of the heel portion can be positioned in sufficient spaced relation to the heel of a user to prevent contact between the inner surface of the heel portion and the heel of the user thereby to eliminate any chafing, or abrasive contact, or decubitus or pain-inducing pressure between the heel of the user and the inner surface of the heel portion. The side margins of the heel portion are adapted to receive releasable fastening members for engaging the foot of a user whereby the inner surface of the heel portion will be maintained in a stable, fixed position in spaced relation to the heel of a user. A one-piece liner is secured to the inside of the device which acts to provide both optimum comfort to the user and to aid in maintaining the foot of a user in the stable, fixed position established by the releasable fastenings carried on the side margins of the heel portion.

9 Claims, 3 Drawing Sheets

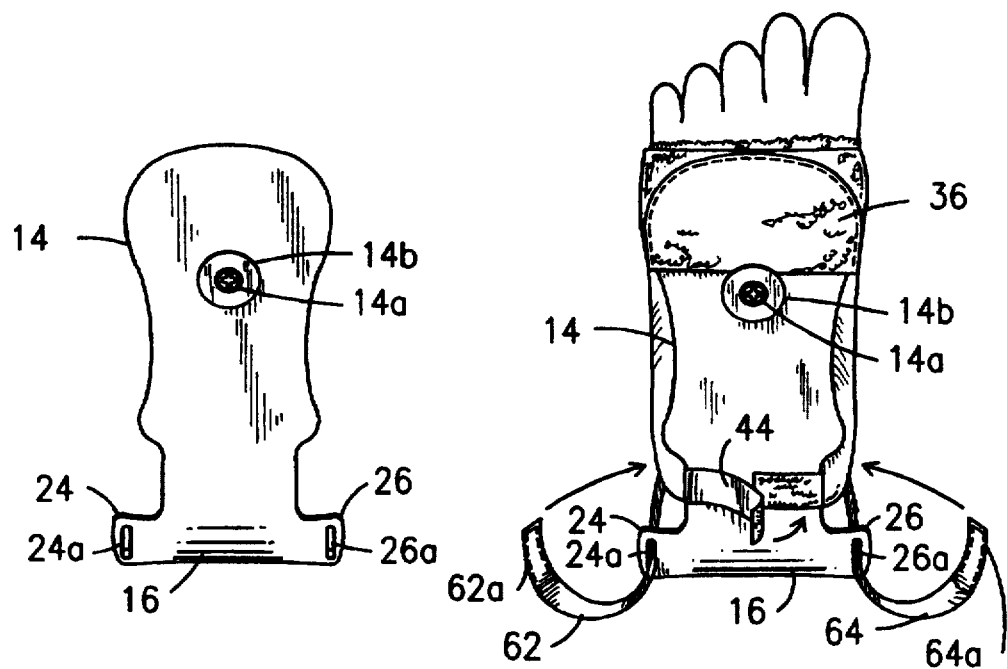
Fig. 3
Fig. 4
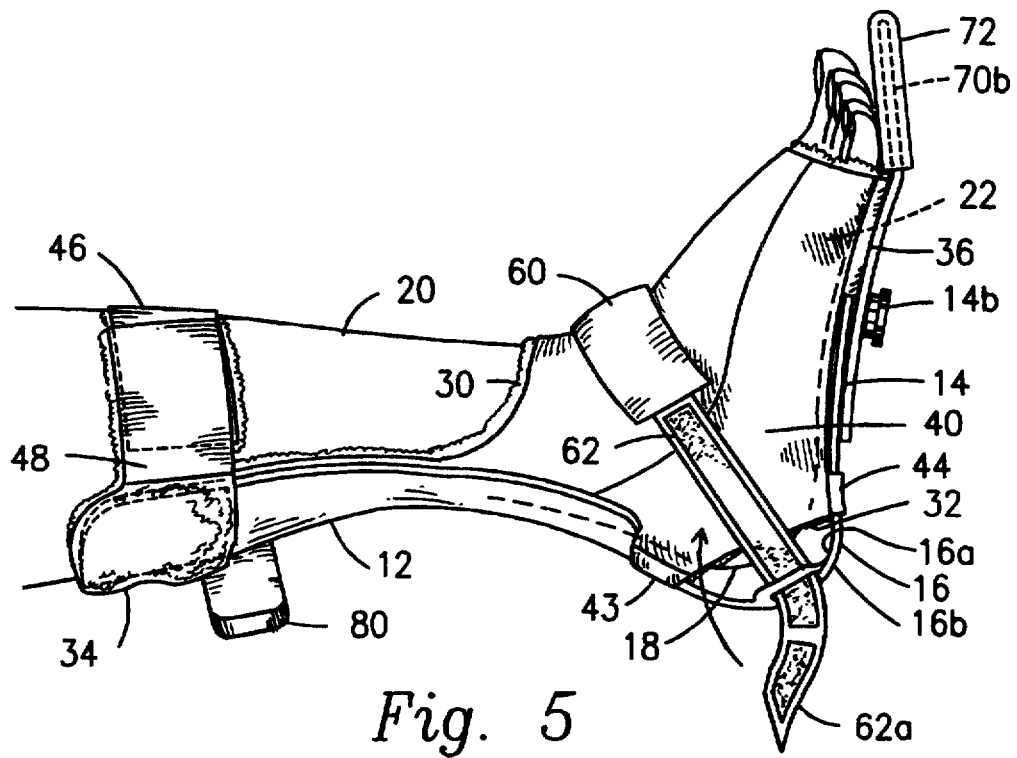
Fig. 5

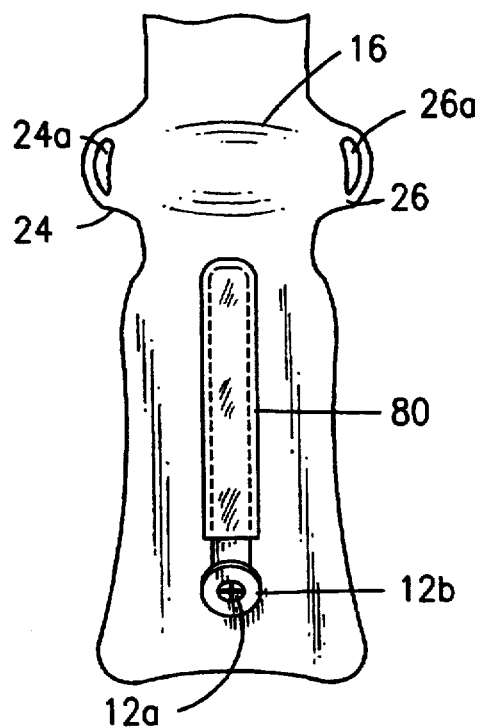
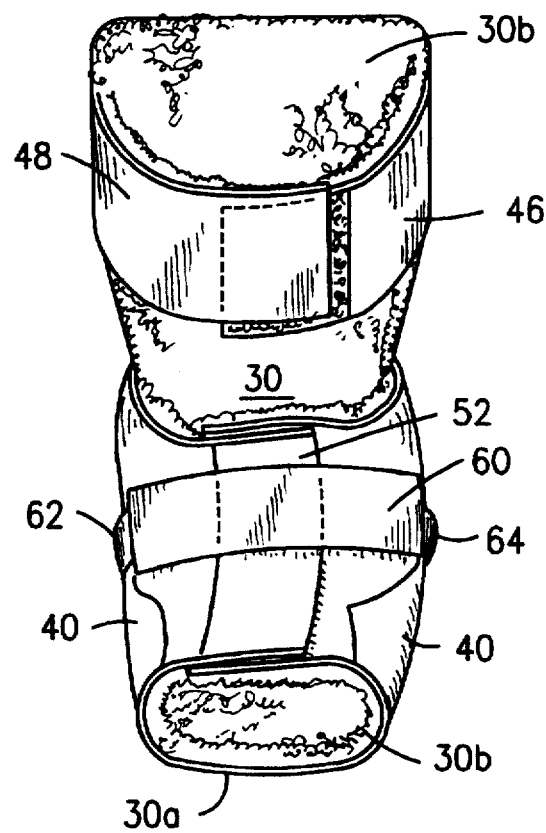
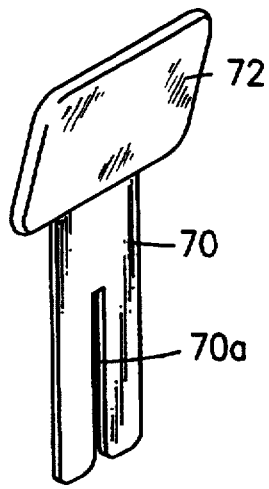
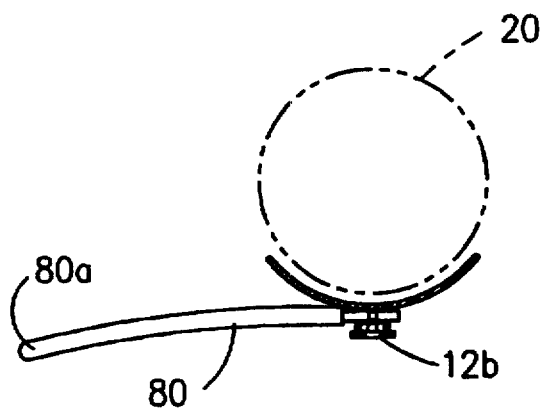
Fig. 6
Fig. 7
Fig. 8
Fig. 9

THERAPEUTIC FOOT ORTHOSIS

This invention relates to a foot orthosis. More particularly, it relates to an improved foot orthosis for firmly positioning the heel of a patient in a manner to avoid pressure on a patient's heel.

BACKGROUND OF THE INVENTION

U.S. Pat. No. 3,976,059 shows a leg and foot device for therapeutic use. The device comprises a leg engaging portion, a foot portion and a curved, narrow heel portion providing an integral connection between the leg and foot portions. While the patent states that the heel portion is curved to avoid contact with a patient's heel, the curvature is inadequate to prevent the heel of a patient from coming into contact with the heel portion under the weight of the foot especially when the patient is in a prone position. Further, in this same connection, no means is provided for the device shown in the patent for maintaining the heel of a patient in a fixed, stable position in spaced relation to the curved heel portion of the device. The inadequacies of the patented device in this regard are further aggravated by the fact that the liner of the device is formed of separate pieces of a cushioning material. This arrangement does not provide the required surface contact between the foot of a patient and %he cushioning material to resist the weight of the foot from bringing the heel of a patient into contact with the curved heel portion of the device.

SUMMARY OF THE INVENTION

The improved therapeutic device of the present invention effectively overcomes all of the aforementioned shortcomings of the device shown in U.S. Pat. No. 3,976,059. In a preferred embodiment of the invention, the device includes a leg engaging portion, a foot supporting portion, and a heel portion which interconnects the leg and foot portions, and, advantageously, is integral therewith. As in the device of said patent, means is provided for releasably attaching the leg and foot portions on a lower extremity of a user. The heel portion of the present invention, in sharp contrast to the device shown in U.S. Pat. No. 3,976,059, has a curvature which permits the inner surface of the heel portion to be positioned in sufficient spaced relation to the heel of a user to prevent contact between the inner surface of the heel portion and heel of the user. The spacing between the inner surface of the heel portion and the heel of a user advantageously is maintained and stabilized by providing the side margins of the heel portion with means for receiving releasable fastening means carried on a foot engaging member which overlies the foot of a user. A one-piece, cushioned liner is attached to the inside of the device which acts, in cooperation with the releasable fastening means carried by the foot engaging member, to aid in maintaining the heel of a user in a stable, fixed position in relation to the inner surface of the heel portion, while at the same time providing optimum comfort to the user. The outer surface of the heel portion presents a wide area of contact with a supporting surface for the device thereby resisting the tendency of the user's foot to move outwardly or laterally when the user is in a prone position. The arrangement of the interacting elements of the device of this invention substantially eliminates any chafing, abrasive contact, or decubitus - or pain-inducing pressure between the heel of a user and the heel portion of the device with the result that correction of foot deformities, and/or the healing of surgical corrective procedures are unimpeded and patient recovery times are reduced.

DESCRIPTION OF THE DRAWINGS

FIG. 3 is a bottom view in elevation of the foot supporting portion of the structure shown in FIG. 1;

FIG. 4 is a bottom view of the embodiment of the device shown in FIG. 2 with the foot of a user in position on the foot supporting portion;

FIG. 5 is a side view in elevation showing said embodiment of the device positioned on a lower extremity of a user;

FIG. 6 is a fragmentary rear view in elevation of said embodiment of the device;

FIG. 7 is a front view in elevation of the embodiment of the device shown in FIG. 2 with the cushioned liner in its closed condition;

FIG. 8 is a perspective view of the adjustable toe engaging attachment carried on the underside of the foot supporting portion of the structure shown in FIG. 1; and FIG. 9 is a front view, partly in section, showing the leg stabilizing post or stand carried on the leg engaging portion of the support structure shown in FIG. 1 in its extended position.

DESCRIPTION OF THE INVENTION

Figure 1:
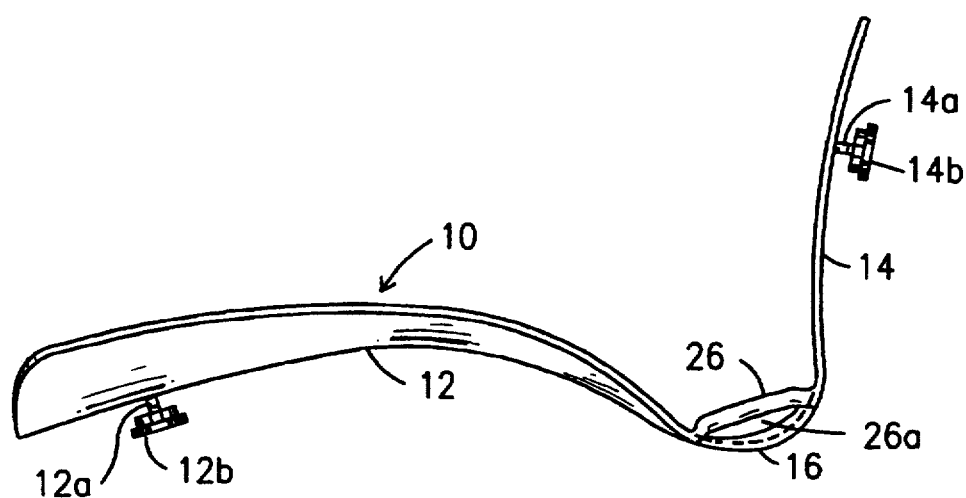
FIG. 1 is a side view in elevation of the support structure of the device of the present invention.

The support structure shown in FIG. 1, and designated generally by reference numeral 10, comprises a leg engaging portion 12, a foot supporting portion 14, and an interconnecting, integral heel portion 16. The structure 10 advantageously is contoured and shaped to enable the device of the present invention to be readily and comfortably attached to the leg and foot of a user, and desirably is formed as a one-piece unit from a plastic material exemplified by a flexible high impact strength polyethylene, polypropylene, polymethylmethacrylate, or the like. The thickness of the structure 10 should be such that it will have sufficient flexibility to enable the device to both conform to the leg and foot of a user while at the same time permitting limited movement of the lower extremities. As shown in FIG. 1, the leg engaging portion 12 is provided with an externally threaded bolt 12a for receiving a knurled edged nut 12b, and the foot supporting portion 14, similarly, is provided with an externally threaded bolt 14b for receiving a knurled edged nut 14b, the function of each of which will become clear as the description proceeds.

As best illustrated in FIGS. 3, 4, 5 and 6 of the drawings, the heel portion 16 of the structure 10 is wider than the foot supporting portion 14, and has a curvature such that the inner surface 16a of the heel portion 16 is positioned in appreciable spaced relation with respect to the heel 18 of a user when the device is attached to the leg 20 and foot 22 of a user. In the embodiment shown, the heel portion 16 of the structure 10 advantageously is provided with a lateral extension 24 and a lateral extension 26 having slots 24a and 26a, respectively, formed therein, the function of which will be made clear as the description proceeds.

Figure 2:
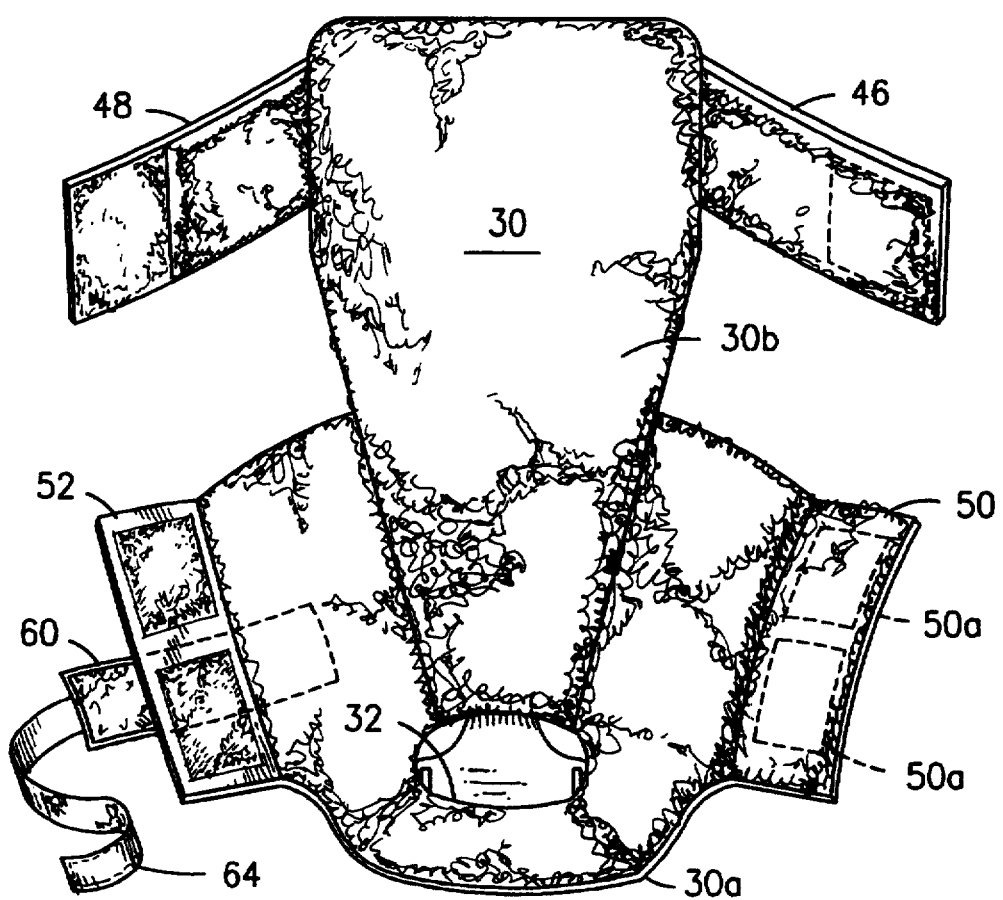
FIG. 2 is a front view in elevation of an embodiment of the device showing it in its open condition ready to receive a lower extremity of a user.

In a preferred embodiment of the invention and as best illustrated in FIGS. 2 and 7, the device is provided with a one-piece liner 30 which overlies the inner surface of the leg engaging portion 12 and the foot supporting portion 14 of the structure 10. The liner 30 desirably is formed of a stretchable, fabric backing 30a to which is applied a soft, pliable nap or facing 30b formed of a sheared plastic material such as nylon, a polyester, a polyacrylic, polyurethane, or the like. The liner 30 is provided with an opening 32 to accommodate the heel of a user when the device is attached to the leg and foot of the user.

As shown in FIGS. 4, and 5, the liner 30 has a pocket 34 provided at one end for receiving the upper marginal area of the leg engaging portion 12, and a pocket 36 for receiving the forward end of the foot supporting portion 14 of the structure 10. The pocket 36 desirably is formed by a reinforcing layer or panel 40 secured as by stitching to the backing 30a of the liner 30 along each side of the liner 30 adjacent to the side edges of the foot supporting portion 14. The reinforcing layer or panel 40 advantageously extends along the margins of the liner 30 which define the heel receiving opening 32 formed therein to provide added support for maintaining the heel 18 of a user in fixed, stable, spaced relation to the inner surface 16a of the heel portion 16 of the structure 10.

Straps 43 and 44 (see FIGS. 4 and 5) provided with releasable fastening means desirably of the hook and loop type, are secured to the liner 30 on opposite sides of the opening 32 for attaching the liner 30 to the lower end of the leg engaging portion 12 and to the inner end of the foot supporting portion 14 in proximity to the heel portion 16.

The upper end of the liner 30 is provided with releasably connectable straps 46 and 48 which are adapted to overlie the leg of a user as shown in FIG. 5. Fastening means of the hook and loop type can be used to secure the straps 46 and 48 in overlying relation to one another. The liner 30 further is formed to provide an extension or flap 50 adapted to overlie the foot 22 of a user. The outer surface of the flap 50 carries areas or patches 50a—50a of a heavy duty fabric, exemplified by nylon, having releasable fastening means of the hook type provided thereon which cooperate with releasable fastening means of the loop type provided on one surface of an elongated strip 52 of a heavy duty fabric secured as by stitching to the outer margin of the foot engaging portion of the liner 30 opposite to that on which the flap 50 is carried.

Referring now, in particular to FIGS. 2, 4, 5, 6 and 7 of the drawings, the heel 18 of a user is maintained in fixed, stable, spaced relation to the inner surface 16 of the heel portion 16 of the structure 10 by means of a padded member 60 secured at one of its ends to a strap 62 attached as by stitching to the reinforcing layer 40 provided on the backing of the liner 30 adjacent to the opening 32 formed therein. The free end 62a of the strap 62 is adapted to pass through the slot 26a formed in the extension 26 of the heel portion 16 of the structure 10, and to be folded back in superimposed relation on the area of the strap 62 which is secured to the reinforcing layer 40. The strap 62 desirably is provided with releasable fastening means of the hook and loop type to enable the free end 62a thereof to be disengaged from the heel portion 16. The other end of the padded member 60 has a strap 64 secured thereto, the free end 64a thereof being adapted to pass through the slot 24a formed in the extension 24 of the heel portion 16, and, like the free end 62a of the strap 62, to be folded back in superimposed relation on itself. As with the strap 62, the strap 64 is provided with releasable fastening means of the hook and loop type to enable the free end 64a thereof to be disengaged from the heel portion 16.

As shown in FIGS. 5 and 7 of the drawings, the padded member 60 snugly overlies the foot engaging portion of the liner 30 when the straps 62 and 64 are connected to the extensions 24 and 26 of the heel portion 16. This arrangement acts to prevent the heel 18 of a user of the device from coming into contact with the inner surface 16a of the heel portion 16. The fixed, stable position of the heel portion 16 in relation to the heel 18 of a user is enhanced, augmented and promoted by the reinforced areas of the panel 40 which are positioned along the edges of the heel accommodating opening 32 formed in the liner 30. These features of the device of this invention effectively prevent heel decubitus from occurring, and can aid in the healing of such a condition in the event it has occurred for some other reason. The fixed, stable, spaced positioning of the heel of a user with relation to heel portion 16 of the device also enables observation during healing of any surgical procedures performed on the heel of the user, and enables heavier, more absorbent bandaging materials to be used on incisions made during such procedures.

The device further advantageously incorporates auxiliary means for promoting its effective use in treating foot problems. To this end, an adjustable extension 70 is carried on the foot supporting portion 14. The foot portion 14 normally has a length which is not equal to the length of the foot 22 of the user. The extension 70 is provided with an open-ended elongated slot 70a in which the externally threaded bolt 14b rides. The extension 70 can be locked in a desired position with relation to toes of the user's foot by means of the lock nut 14b. The leading end 70b of the extension 70 is bent upwardly and desirably is provided with a cushioned cover 72. The extension 70 can function to act as support for the toes when the user is sitting, or when he is ambulatory. It can also function, in its fully extended position, to prevent bed sheets or blankets from exerting any weight on the foot of a user.

In this same connection, the leg engaging portion 12 of the device of this invention is provided with a leg stabilizing post or stand 80 which is rotatably engaged on the bolt 12a secured to the leg engaging portion 12. As shown in FIG. 9, rotation of the stand 80 at approximately a 90 degree angle to the longitudinal axis of the leg engaging portion 12 prevents the leg of a user from rotating. This is especially important in conditions which afflict certain stroke victims. The stand 80 desirably is provided with non-abrasive cover 80a to cushion any possible contact between the stand 80 and the leg of a user.

In those instances where severe rotation of the leg is not a problem, the outer surface 16b of the heel portion 16 provides a relatively large area of contact with a supporting surface such as bedding when the user of the device is in a prone position. As a result, unlike the essentially point-contact provided by the heel portion of U.S. Pat. No. 3,976,059, rotation of the leg is resisted, and the foot of a user can more easily be maintained in an upright position.

While there has been herein shown and described a preferred embodiment of the present invention, it should be understood the invention may be embodied otherwise than is herein illustrated and described, and that in said embodiments, certain changes in the detailed construction, and in the form and arrangement of parts may be made without departing from the underlying idea or principles of this invention within the scope of the appended claims.

I claim:

1. In a therapeutic device for attachment to the leg and foot of a user, said device including a leg engaging portion, a foot supporting portion, and a heel portion interconnecting the leg and foot portions, and further including means for releasably attaching the leg and foot portions on a leg of a user, the improvement wherein the heel portion interconnecting the leg and foot portions has an inner and an outer surface and an outward curvature between the leg and foot portions which enables the inner surface of the heel portion to be positioned in sufficient spaced relation to the heel of a user to prevent contact between said inner surface of the heel portion and heel of a user, and a releasable foot engaging member adapted to overlie the foot of a user, said foot engaging member having adjustable fastening means connectable to opposed laterally extending projections from the heel portion whereby the inner surface of the heel portion will be maintained in a stable, fixed position in spaced relation to the heel of a user.

2. A therapeutic device according to claim 1 wherein the opposed laterally extending projections from the heel portion has an opening provided along each of a distal side margin, each of said openings receiving the adjustable fastening means of the foot engaging member.

3. A therapeutic device according to claim 2 wherein each of the openings on the heel portion is an elongated slot for receiving the adjustable fastening means of the foot engaging member.

4. A therapeutic device according to claim 1 wherein the foot engaging member comprises a cushioned portion adapted to overlie the foot of a user, and releasable strap means for connecting the foot engaging member to the heel portion.

5. A therapeutic device according to claim 1 wherein a one-piece liner is provided for the leg engaging portion and the foot supporting portion, the liner having an opening for receiving the heel of a user.

6. A therapeutic device according to claim 5 wherein the liner has a reinforcing panel secured on the outer surface thereof, an area of said panel being located along the periphery of the heel receiving opening in the liner and acting in cooperation with the foot engaging member to maintain the heel of a user in a stable, fixed position.

7. A therapeutic device according to claim 6 wherein one end of the foot engaging member is anchored on the reinforcing panel.

8. A therapeutic device according to claim 1 wherein the laterally extending projections on the heel portion enlarge the area of the outer surface of the heel portion thereby to provide greater contact between the outer surface of the heel portion and a supporting surface for the device when a user is in a prone position.

9. A therapeutic device for attachment to the legs and foot of a user, said device including a leg engaging portion, a foot supporting portion, and a heel portion integral with the leg engaging and foot supporting portions, and further including releasable strap means for attaching the device on the leg and foot of a user, the improvement wherein the heel portion has an inner and an outer surface and an outward curvature between the leg and foot portions which enables the inner surface of the heel portion to be positioned in sufficient spaced relation to the heel of a user to prevent contact between said inner surface and the heel of a user, opposed lateral side extensions on said heel portion provided with strap receiving slots, a releasable foot engaging member adapted to overlie the foot of a user, said foot engaging member carrying releasable straps for engagement in the slots in the side extensions of the heel portion, and a one-piece liner for the leg engaging and foot supporting portions of the device, said liner having an opening formed therein for receiving the heel of a user, the outer periphery of the opening being reinforced and acting in cooperation with the releasable foot engaging means to maintain the heel of a user in a stable, fixed position in spaced relation to the heel of a user.

* * * * *